United States Patent
Moriya

(10) Patent No.: US 10,448,816 B2
(45) Date of Patent: Oct. 22, 2019

(54) LIGHT SOURCE APPARATUS, ENDOSCOPE SYSTEM AND OPERATING METHOD

(71) Applicant: FUJIFILM Corporation, Tokyo (JP)

(72) Inventor: Yoshiyuki Moriya, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1408 days.

(21) Appl. No.: 14/497,673

(22) Filed: Sep. 26, 2014

(65) Prior Publication Data
US 2015/0094530 A1 Apr. 2, 2015

(30) Foreign Application Priority Data

Sep. 27, 2013 (JP) .................................. 2013-201500

(51) Int. Cl.
| | | |
|---|---|---|
| A61B 1/06 | (2006.01) | |
| A61B 1/00 | (2006.01) | |
| F21K 9/61 | (2016.01) | |
| F21Y 115/10 | (2016.01) | |

(52) U.S. Cl.
CPC ........ *A61B 1/0638* (2013.01); *A61B 1/00009* (2013.01); *A61B 1/0005* (2013.01); *F21K 9/61* (2016.08); *F21Y 2115/10* (2016.08)

(58) Field of Classification Search
CPC . A61B 1/00009; A61B 1/0005; A61B 1/0638; F21K 9/61; F21V 33/0068; F21W 2131/20; F21Y 2105/00; F21Y 2115/10; G02B 6/0001
See application file for complete search history.

(56) References Cited

U.S. PATENT DOCUMENTS

| | | | |
|---|---|---|---|
| 8,531,512 B2 | 9/2013 | Gono et al. | |
| 2007/0153542 A1* | 7/2007 | Gono | A61B 1/0638 362/574 |
| 2008/0239070 A1* | 10/2008 | Westwick | A61B 1/045 348/68 |
| 2009/0181339 A1* | 7/2009 | Liang | A61B 1/0638 433/29 |
| 2010/0240953 A1* | 9/2010 | Murakami | A61B 1/0005 600/109 |
| 2010/0278404 A1* | 11/2010 | Takei | A61B 1/0638 382/128 |

(Continued)

FOREIGN PATENT DOCUMENTS

JP 2002-209839 A 7/2002

*Primary Examiner* — Aaron B Fairchild
(74) *Attorney, Agent, or Firm* — Birch, Stewart, Kolasch & Birch, LLP

(57) ABSTRACT

A light source apparatus for endoscopic imaging includes a light source for emitting at least narrow band blue light and narrow band green light, to illuminate an object in a body cavity. The light source is changeable over between field sequential lighting and simultaneous lighting. The light source, upon setting of the field sequential lighting, emits the narrow band blue light and narrow band green light in a discrete manner, and upon setting of the simultaneous lighting, simultaneously emits the narrow band blue light and narrow band green light. A connector is connectable with an endoscope having a complementary color image sensor of yellow, magenta and cyan, for imaging the object. A controller sets the field sequential lighting assuming that the endoscope is connected to the light source and assuming that the light source is used for emitting the narrow band blue light and narrow band green light.

5 Claims, 13 Drawing Sheets

(56) References Cited

U.S. PATENT DOCUMENTS

| | | | |
|---|---|---|---|
| 2011/0112362 A1* | 5/2011 | Minetoma | A61B 1/05 600/109 |
| 2011/0230715 A1* | 9/2011 | Saito | A61B 1/00009 600/109 |
| 2011/0245642 A1* | 10/2011 | Minetoma | A61B 1/0638 600/324 |
| 2012/0127292 A1* | 5/2012 | Yamazaki | A61B 1/00009 348/68 |
| 2012/0157774 A1* | 6/2012 | Kaku | A61B 1/0005 600/178 |
| 2012/0157775 A1* | 6/2012 | Yamaguchi | A61B 1/0638 600/180 |
| 2012/0165627 A1* | 6/2012 | Yamamoto | A61B 1/043 600/317 |
| 2012/0179050 A1* | 7/2012 | Saito | A61B 1/00009 600/476 |
| 2012/0190922 A1* | 7/2012 | Kaku | A61B 1/00009 600/109 |
| 2012/0197076 A1* | 8/2012 | Minetoma | A61B 1/00009 600/109 |
| 2012/0197077 A1* | 8/2012 | Kaku | A61B 1/00009 600/109 |
| 2012/0218394 A1* | 8/2012 | Yoshino | A61B 1/0005 348/65 |
| 2012/0220840 A1* | 8/2012 | Morita | A61B 1/00009 600/317 |
| 2012/0241620 A1* | 9/2012 | On | A61B 1/00172 250/338.1 |
| 2012/0242859 A1* | 9/2012 | Sasaki | A61B 1/00165 348/223.1 |
| 2012/0253122 A1* | 10/2012 | Minetoma | A61B 1/00057 600/109 |
| 2012/0259232 A1* | 10/2012 | Minetoma | A61B 1/00009 600/479 |
| 2012/0310047 A1* | 12/2012 | Kasamatsu | A61B 1/0638 600/178 |
| 2013/0006109 A1* | 1/2013 | Takei | A61B 1/00009 600/432 |
| 2013/0041218 A1* | 2/2013 | Iida | A61B 1/0638 600/109 |
| 2013/0053646 A1* | 2/2013 | Yamamoto | A61B 1/043 600/180 |
| 2013/0053703 A1* | 2/2013 | Yamamoto | A61B 1/0638 600/476 |
| 2013/0070071 A1* | 3/2013 | Peltie | A61B 1/05 348/68 |
| 2013/0176411 A1* | 7/2013 | Igarashi | G02B 23/2484 348/65 |
| 2013/0265401 A1* | 10/2013 | Igarashi | A61B 1/0661 348/68 |

* cited by examiner

FIG. 7

| ENDOSCOPE TYPE | IMAGING MODE | LIGHTING CONTROL |
|---|---|---|
| 1ST ENDOSCOPE (COMPLEMENTARY COLORS) | NORMAL LIGHT | SIMULTANEOUS LIGHTING |
| | NARROW BAND LIGHT | FIELD SEQUENTIAL LIGHTING |
| 2ND ENDOSCOPE (THREE PRIMARY COLORS) | NORMAL LIGHT | SIMULTANEOUS LIGHTING |
| | NARROW BAND LIGHT | SIMULTANEOUS LIGHTING |
| 3RD ENDOSCOPE (MONOCHROMATIC) | NORMAL LIGHT | FIELD SEQUENTIAL LIGHTING |
| | NARROW BAND LIGHT | FIELD SEQUENTIAL LIGHTING |

FIG. 8

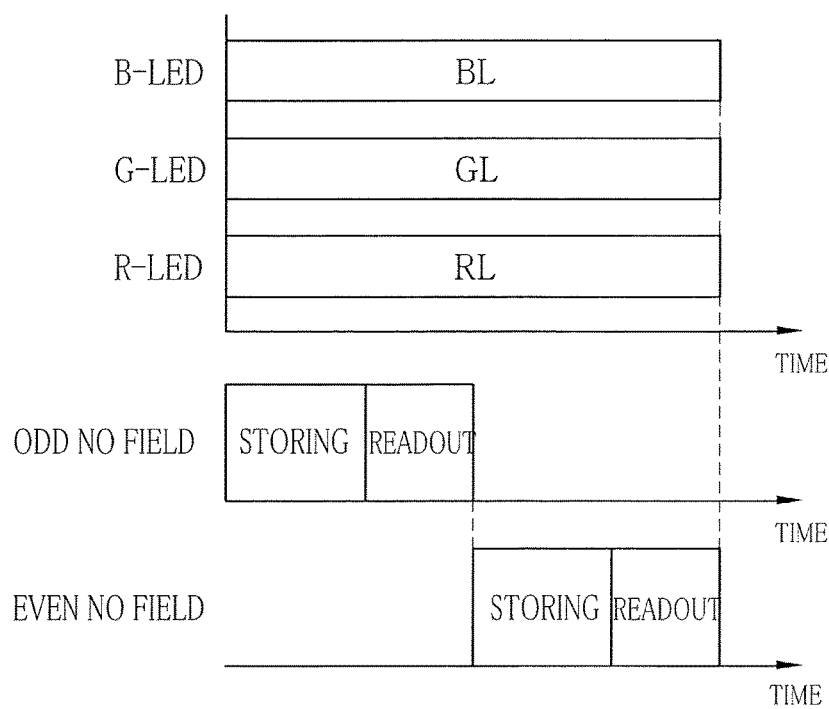

LIGHT SOURCE APPARATUS, ENDOSCOPE SYSTEM AND OPERATING METHOD

CROSS-REFERENCE TO RELATED APPLICATION

This application claims priority under 35 USC 119 from Japanese Patent Application No. 2013-201500, filed 27 Sep. 2013, the disclosure of which is incorporated by reference herein.

BACKGROUND OF THE INVENTION

1. Field of the Invention

The present invention relates to a light source apparatus, an endoscope system and an operating method. More particularly, the present invention relates to a light source apparatus in which field sequential lighting and simultaneous lighting are changeable, and performance of color separation can be high typically for imaging with narrow band light, an endoscope system and an operating method.

2. Description Related to the Prior Art

An endoscope system is well-known in the field of medical diagnosis, and includes a light source apparatus, an electronic endoscope and a processing apparatus. The light source apparatus emits light for illumination to an object of interest in a body cavity. An image sensor in the endoscope images the object of interest illuminated with the light, and generates an image signal. The processing apparatus processes the image signal in image processing, and generates an image for display on a monitor display panel.

Two lighting controls are available in the endoscope system, including field sequential lighting and simultaneous lighting. In the field sequential lighting, red (R), green (G) and blue (B) light components are applied to the object of interest sequentially one after another. A monochromatic image sensor images the object of interest illuminated with the light components in sequential steps. In the simultaneous lighting, red (R), green (G) and blue (B) light components are applied to the object of interest simultaneously, so that white light is applied thereto. A multi-color image sensor for use with simultaneous lighting is used, has a color filter, and images the object of interest illuminated with the white light.

The field sequential lighting generates one image by imaging of three frames with the monochromatic image sensor, and has a feature of high spatial resolution and low time resolution. In contrast, the simultaneous lighting generates one image by imaging of one frame with the multi-color image sensor, and has a feature of high time resolution and low spatial resolution.

In short, the field sequential lighting and the simultaneous lighting have the features distinct from one another. In consideration of this, there is a type of the endoscope system as disclosed in JP-A 2002-209839 in which first and second endoscopes are selectively usable. The first endoscope has the monochromatic image sensor. The second endoscope has the multi-color image sensor. Any one of the first and second endoscopes is connected to the light source apparatus and the processing apparatus. The endoscope system is switchable to set the field sequential lighting upon connecting the first endoscope, and to set the simultaneous lighting upon connecting the second endoscope.

Examples of the multi-color image sensor include a three primary color image sensor or first multi-color image sensor with a three primary color separation filter (of red, green and blue), and a complementary color image sensor or second multi-color image sensor with a complementary color separation filter (of yellow, magenta and cyan). The three primary color image sensor has a lower sensitivity than the complementary color image sensor, but has a better performance of color reproduction than the complementary color image sensor, and is typically used in the endoscope system with higher importance in the color. The three primary color image sensor has a poorer performance of color reproduction than the complementary color image sensor, but has a higher sensitivity than the complementary color image sensor, and is typically used in the endoscope system with higher importance in the sensitivity.

In addition to the normal imaging with white light in the endoscope system, there is a method of narrow band imaging mode in which narrow band light with a narrow wavelength range is used for imaging. The narrow band imaging mode is characterized in imaging the object of interest with surface blood vessels in body tissue with good visual recognition in contrast with normal imaging in which the surface blood vessels with may not be recognized in optical information. It is possible in the narrow band imaging mode to diagnose progress of a lesion in the surface blood vessels, penetration depth of the lesion and the like by sharply imaging the surface blood vessels.

In the narrow band imaging mode, narrow band blue light and narrow band green light are used as light components easily absorbable in hemoglobin in blood. The narrow band blue light has a center wavelength of approximately 415 nm. The narrow band green light has a center wavelength of approximately 540 nm. Furthermore, there are two lighting controls in the narrow band imaging mode, including the field sequential lighting in combination with the monochromatic image sensor, and the simultaneous lighting in combination with the multi-color image sensor, as disclosed in U.S. Pat. No. 8,531,512 (corresponding to JP-B 4009626).

In the narrow band imaging mode of the endoscope system, the narrow band blue light and the narrow band green light are detected discretely by blue and green pixels in the three primary color image sensor. It is possible to obtain an image with good visual recognition of the surface blood vessels, namely, contrast between the surface blood vessels and mucosa, owing to distinct color separation. However, the complementary color image sensor detects the narrow band blue light and the narrow band green light simultaneously with common pixels, so that color mixture occurs. There is a problem in that visual recognition of the surface blood vessels may be poor due to low performance in the color separation.

SUMMARY OF THE INVENTION

In view of the foregoing problems, an object of the present invention is to provide a light source apparatus in which field sequential lighting and simultaneous lighting are changeable, and performance of color separation can be high typically for imaging with narrow band light, an endoscope system and an operating method.

In order to achieve the above and other objects and advantages of this invention, a light source apparatus for endoscopic imaging includes a light source for emitting at least first narrow band light and second narrow band light having a longer wavelength than the first narrow band light to illuminate an object in a body cavity, the light source being changeable over between field sequential lighting and simultaneous lighting, wherein the light source, upon setting of the field sequential lighting, emits the first narrow band light and the second narrow band light in a discrete manner, and upon setting of the simultaneous lighting, simultaneously emits the first narrow band light and the second narrow band light. A connector is connectable with a first endoscope having a complementary color image sensor for imaging the object. A controller sets the field sequential lighting assuming that the first endoscope is connected to the light source and assuming that the light source is used for emitting the first narrow band light and the second narrow band light.

Preferably, the controller selectively specifies first and second emission sequences in the field sequential lighting, and in the first emission sequence, the first narrow band light and the second narrow band light are alternately emitted, and in the second emission sequence, two events of emitting the first narrow band light and one event of emitting the second narrow band light are alternately repeated.

Preferably, the controller operates according to a brightness signal of object brightness of the object, and assuming that the object brightness is higher than reference brightness, specifies the first emission sequence in the field sequential lighting, and assuming that the object brightness is equal to or lower than the reference brightness, specifies the second emission sequence in the field sequential lighting.

Preferably, the controller controls light intensity of the light source according to information of a difference between the object brightness and the reference brightness, and assuming that the light intensity comes up to a peak intensity, changes over the field sequential lighting from the first emission sequence to the second emission sequence.

Preferably, the complementary color image sensor has pixels of at least yellow, magenta and cyan colors.

Preferably, the first narrow band light is narrow band blue light, and the second narrow band light is narrow band green light.

Also, an endoscope system is provided, and includes a first endoscope, having a complementary color image sensor, for imaging an object in a body cavity. A light source apparatus illuminates the object, the light source apparatus being changeable over between field sequential lighting and simultaneous lighting in a narrow band imaging mode, wherein the light source apparatus, upon setting of the field sequential lighting, emits first narrow band light and second narrow band light having a longer wavelength than the first narrow band light in a discrete manner, and upon setting of the simultaneous lighting, simultaneously emits the first narrow band light and the second narrow band light. A controller sets the field sequential lighting assuming that the first endoscope is connected to the light source apparatus and upon setting of the narrow band imaging mode. An image signal processor generates first and second image data according to an output signal from the complementary color image sensor upon imaging by use of the first narrow band light and the second narrow band light, to produce a special image by combining the first and second image data.

Preferably, the first narrow band light and the second narrow band light are alternately emitted in a first emission sequence in the field sequential lighting. The image signal processor combines the first and second image data at each time that the first or second image data is generated in the first emission sequence.

Preferably, in a second emission sequence, two events of emitting the first narrow band light and one event of emitting the second narrow band light are alternately repeated in the field sequential lighting. The image signal processor combines two sets of the first image data and one set of the second image data at each time that the first or second image data is generated in the second emission sequence.

Preferably, furthermore, a brightness detector detects object brightness of the object according to the output signal.

The controller, assuming that the object brightness is higher than reference brightness, specifies the first emission sequence in the field sequential lighting, and assuming that the object brightness is equal to or lower than the reference brightness, specifies the second emission sequence in the field sequential lighting.

In another preferred embodiment, furthermore, a brightness detector detects object brightness of the object according to the output signal. A light adjuster outputs an adjustment signal according to the object brightness and reference brightness. The controller adjusts light intensity of the light source apparatus according to the adjustment signal so as to set the object brightness equal to the reference brightness.

Preferably, furthermore, a brightness detector detects object brightness of the object according to the output signal. Assuming that the light intensity comes up to a peak intensity according to the object brightness, the controller changes over the field sequential lighting from the first emission sequence to the second emission sequence.

Preferably, the controller in the first emission sequence sets a light amount of the first narrow band light higher than a light amount of the second narrow band light by controlling the light source apparatus.

Preferably, the light source apparatus includes plural first light source devices for emitting the first narrow band light. At least one second light source device emits the second narrow band light. In the first emission sequence, the plural first light source devices are used together to set a light amount of the first narrow band light higher than a light amount of the second narrow band light.

Preferably, the light source apparatus is changeable over between the field sequential lighting and the simultaneous lighting in a normal imaging mode, wherein the light source apparatus, upon setting of the field sequential lighting, emits red, green and blue light in a discrete manner, and upon setting of the simultaneous lighting, simultaneously emits the red, green and blue light. The controller sets the simultaneous lighting assuming that the first endoscope is connected to the light source apparatus and upon setting of the normal imaging mode, and the image signal processor produces a normal image according to the output signal from the complementary color image sensor.

Preferably, assuming that a second endoscope having a three primary color image sensor is connected to the light source apparatus, the controller sets the simultaneous lighting, and the image signal processor produces the normal image or special image according to an output signal from the three primary color image sensor.

Preferably, assuming that an endoscope having a monochromatic image sensor is connected to the light source apparatus, the controller sets the field sequential lighting, and the image signal processor produces the normal image or special image according to an output signal from the monochromatic image sensor.

Preferably, the complementary color image sensor has pixels of at least yellow, magenta and cyan colors.

Also, an operating method for an endoscope system is provided, the endoscope system including an endoscope for imaging an object in a body cavity, and a light source apparatus for illuminating the object, the light source apparatus being changeable over between field sequential lighting and simultaneous lighting, wherein the light source apparatus, upon setting of the field sequential lighting, emits first narrow band light and second narrow band light having a longer wavelength than the first narrow band light in a discrete manner, and upon setting of the simultaneous lighting, simultaneously emits the first narrow band light and the second narrow band light. The operating method includes a step of setting the field sequential lighting assuming that the endoscope having a complementary color image sensor is connected to the light source apparatus. First and second image data are generated according to an output signal from the complementary color image sensor upon imaging by use of the first narrow band light and the second narrow band light, to produce a special image by combining the first and second image data.

Consequently, performance of color separation can be high typically for imaging with narrow band light, because the use of a complementary color image sensor is recognized and considered for changeover to field sequential lighting.

BRIEF DESCRIPTION OF THE DRAWINGS

The above objects and advantages of the present invention will become more apparent from the following detailed description when read in connection with the accompanying drawings, in which:

FIG. 7 is a table illustrating a relationship between lighting controls and types and imaging modes of endoscopes;

FIG. 8 is a timing chart illustrating a sequence of driving for normal imaging;

DETAILED DESCRIPTION OF THE PREFERRED EMBODIMENT(S) OF THE PRESENT INVENTION

Figure 1:
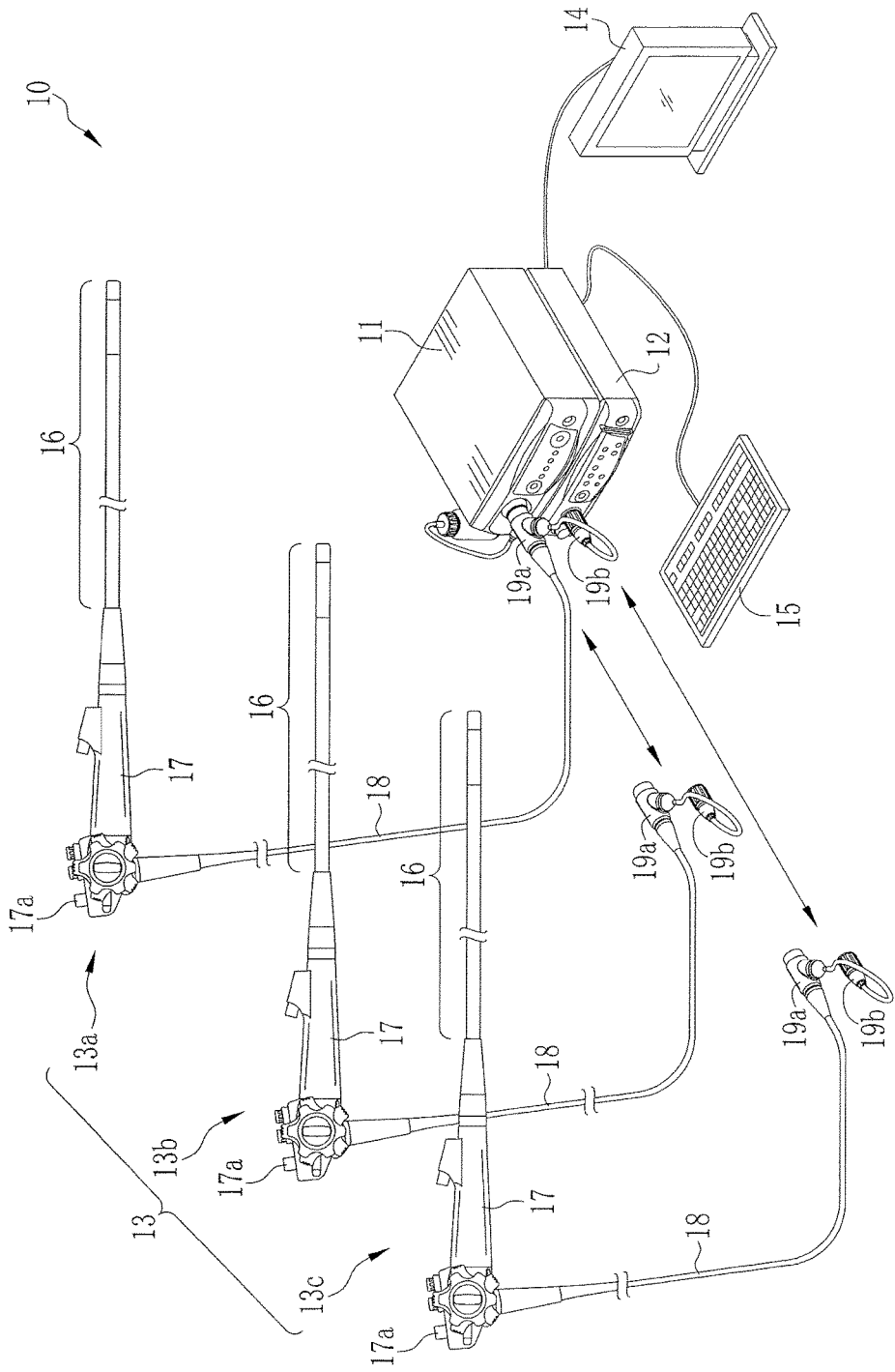
FIG. 1 is an explanatory view illustrating an endoscope system.

In FIG. 1, an endoscope system 10 includes an electronic endoscope 13, a light source apparatus 11 and a processing apparatus 12. The endoscope 13 is connectable to the light source apparatus 11 and the processing apparatus 12 in a removable manner. The light source apparatus 11 generates light for supply to the endoscope 13. A tip of the endoscope 13 is entered in a body cavity of a patient, and images an object of interest in the body cavity. The processing apparatus 12 controls imaging of the endoscope 13, and processes an image signal from the endoscope 13 for image processing.

A display panel 14 and a user input interface 15 are connected to the processing apparatus 12. An example of the display panel 14 is a liquid crystal display panel or the like, and displays an image of an object of interest output by the processing apparatus 12. An example of the user input interface 15 is a keyboard, mouse or the like, and inputs information of various types to the processing apparatus 12.

There are various types of the endoscope 13 connectable to the light source apparatus 11 and the processing apparatus 12. The types include a first endoscope 13a having a complementary color image sensor 28 (or first multi-color image sensor), a second endoscope 13b having a three primary color image sensor 29 (or second multi-color image sensor), and a third endoscope 13c having a monochromatic image sensor 30. The first to third endoscopes 13a-13c are structurally equal except for the image sensors. Each one of the first to third endoscopes 13a-13c includes an elongated tube 16, a grip handle 17, a universal cable 18, a light guide connector 19a and a signal connector 19b.

The elongated tube 16 is a long tube and entered in a body cavity of a patient. The grip handle 17 is disposed at a proximal end of the elongated tube 16, and has a scope switch unit, steering wheels and the like. A mode selector 17a or selection switch is included in the scope switch unit for changing over an imaging mode.

The universal cable 18 extends from the grip handle 17. The light guide connector 19a and the signal connector 19b are disposed at a proximal end of the universal cable 18. The light guide connector 19a is coupled to the light source apparatus 11 in a removable manner. The signal connector 19b is coupled to the processing apparatus 12 in a removable manner.

There are two imaging modes in the endoscope system 10, including a normal imaging mode and a narrow band imaging mode. In the normal imaging mode, red light, green light and blue light as components of white light are applied to an object of interest simultaneously or sequentially, to obtain a normal light image (normal image). In the narrow band imaging mode, narrow band green light (Gn) and narrow band blue light (Bn) as components of narrow wavelength ranges are applied to an object of interest simultaneously or sequentially, to obtain a narrow band light image. The normal imaging mode and the narrow band imaging mode are usable for any one of the first to third endoscopes 13a-13c.

The mode selector 17a described above is operable for selectively setting the normal imaging mode and the narrow band imaging mode. Note that other structures (not shown) can be used for changeover of the imaging modes, for example, a foot switch connected to the processing apparatus 12, a button in a front panel of the processing apparatus 12, the user input interface 15 or the like.

Figure 2:
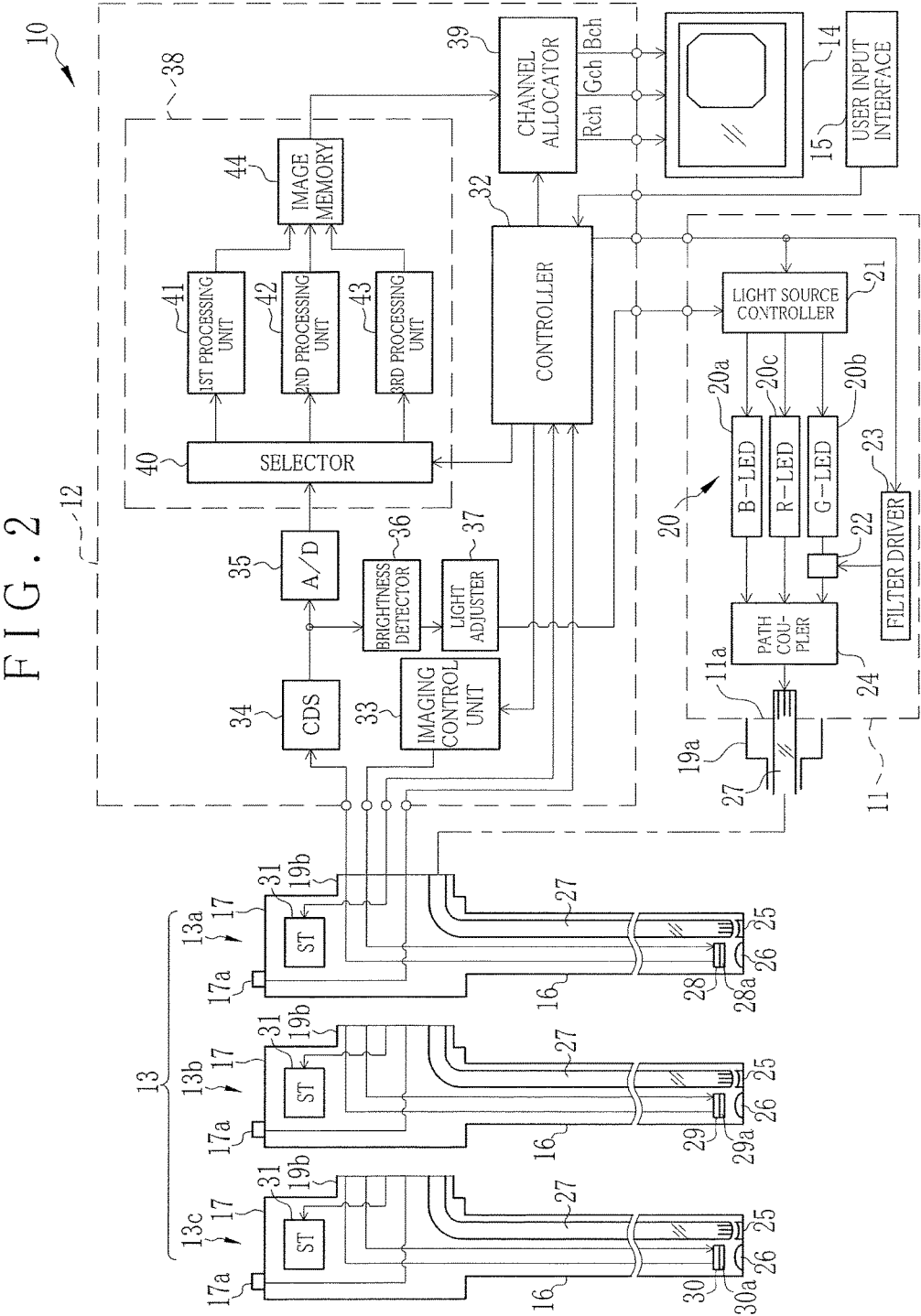
FIG. 2 is a block diagram schematically illustrating the endoscope system.

In FIG. 2, the light source apparatus 11 includes an LED light source 20, a light source controller 21 (controller), a narrow band green filter 22, a filter driver 23 and a path coupler 24. The LED light source 20 includes a blue LED 20a (B-LED or blue light emitting diode), a green LED 20b (G-LED) and a red LED 20c (R-LED) as light source devices.

The blue LED 20a generates blue light BL of a wavelength range of 420-500 nm. The green LED 20b generates green light GL of a wavelength range of 500-600 nm. The red LED 20c generates red light RL of a wavelength range of 600-650 nm.

The light source controller 21 controls turn-on of all the blue, green and red LEDs 20a-20c. In the normal imaging mode, the light source controller 21 drives all the blue, green and red LEDs 20a-20c simultaneously or sequentially to generate normal light. In the narrow band imaging mode, the light source controller 21 drives only the blue and green LEDs 20a and 20b simultaneously or sequentially to generate light.

Two lighting controls (lighting modes) are selectable in the light source controller 21 for the LED light source 20, including simultaneous lighting and field sequential lighting for each of the normal imaging mode and the narrow band imaging mode. In the normal imaging mode and the simultaneous lighting, all the blue, green and red LEDs 20a-20c are turned on simultaneously. In the normal imaging mode and the field sequential lighting, the blue, green and red LEDs 20a-20c are turned on sequentially one after another. In the narrow band imaging mode and the simultaneous lighting, both the blue and green LEDs 20a and 20b are turned on simultaneously. In the narrow band imaging mode and the field sequential lighting, the blue and green LEDs 20a and 20b are turned on sequentially one after another.

The narrow band green filter 22 is shifted into and out of a light path of green light GL from the green LED 20b by the filter driver 23. In the narrow band imaging mode, the narrow band green filter 22 is set in the light path of the green light GL. In the normal imaging mode, the narrow band green filter 22 is set out of the light path of the green light GL. The narrow band green filter 22 passes light of a wavelength range of 530-550 nm.

The blue light BL from the blue LED 20a has such a small half width as 50 nm, and thus is used as narrow band blue light Bn in the narrow band imaging mode. However, the green light GL from the green LED 20b has a large wavelength range, and thus its wavelength range is limited to a width of approximately 20 nm by transmission through the narrow band green filter 22. In the narrow band imaging mode, the green light GL with the limited wavelength range is used as narrow band green light Gn. A central wavelength of the narrow band blue light Bn is approximately 445 nm. A central wavelength of the narrow band green light Gn is approximately 540 nm. Those central wavelengths are included in a wavelength range easily absorbed in hemoglobin in blood for use in the narrow band imaging mode.

Figure 3:
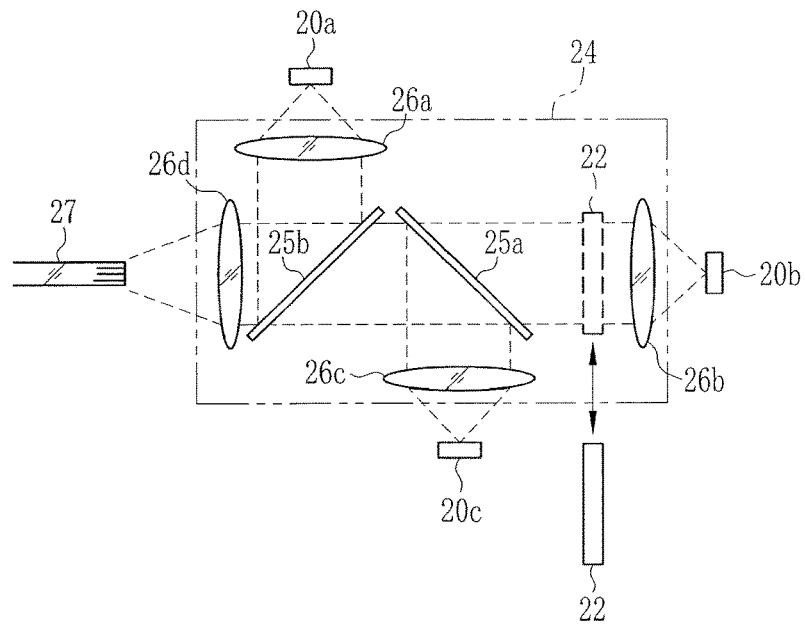
FIG. 3 is a side elevation illustrating a path coupler for coupling light components.

In FIG. 3, the path coupler 24 is constituted by first and second dichroic mirrors 25a and 25b, and a first lens 26a, second lens 26b, third lens 26c and fourth lens 26d. The first, second and third lenses 26a-26c are disposed respectively downstream of the blue, green and red LEDs 20a-20c, and condense light from the blue, green and red LEDs 20a-20c to output parallel light.

A light path of green light GL from the second lens 26b after collimation is perpendicular to a light path of red light RL from the third lens 26c after collimation. The first dichroic mirror 25a is disposed at a point of the intersection of those light paths. The green light GL becomes incident upon one surface of the first dichroic mirror 25a at an angle of 45 degrees. The red light RL becomes incident upon a second surface of the first dichroic mirror 25a at an angle of 45 degrees. The first dichroic mirror 25a has optical property of transmitting the green light GL and reflecting the red light RL. Thus, the green light GL transmitted from the first dichroic mirror 25a is coupled with the red light RL reflected by the first dichroic mirror 25a upon simultaneously turning on the green and red LEDs 20b and 20c.

The light path of the blue light BL from the first lens 26a after collimation is perpendicular to a light path of first mixed light of the green light GL and red light RL. The second dichroic mirror 25b is disposed at a point of the intersection of those light paths. The blue light BL becomes incident upon one surface of the second dichroic mirror 25b at an angle of 45 degrees. The first mixed light becomes incident upon a second surface of the second dichroic mirror 25b at an angle of 45 degrees. The second dichroic mirror 25b has optical property of reflecting the blue light BL and transmitting the first mixed light. Thus, the blue light BL reflected by the second dichroic mirror 25b is coupled with the first mixed light transmitted from the second dichroic mirror 25b. Mixed light after the coupling is condensed by the fourth lens 26d. A light guide device 27 of the endoscope 13 is supplied with the mixed light.

In the normal imaging mode and in the simultaneous lighting, the blue light BL, green light GL and red light RL are combined by the path coupler 24 to output normal light or white light, for entry into the light guide device 27. In the normal imaging mode and in the field sequential lighting, the blue light BL, green light GL and red light RL are generated discretely, for entry into the light guide device 27.

In the narrow band imaging mode and in the simultaneous lighting, the narrow band green filter 22 is set between the second lens 26b and the first dichroic mirror 25a, to combine narrow band blue light Bn from the blue LED 20a with narrow band green light Gn from the narrow band green filter 22, for entry into the light guide device 27. In the narrow band imaging mode and in the field sequential lighting, narrow band blue light Bn and narrow band green light Gn are generated discretely, for entry into the light guide device 27.

There are lighting windows and a viewing window disposed at a distal end of the elongated tube 16 of the endoscope 13. A lighting lens 25 is positioned in each of the lighting windows. An objective lens 26 is positioned in the viewing window. The light guide device 27 extends through the endoscope 13, and has a distal end opposed to the lighting lens 25. A proximal end of the light guide device 27 is disposed in the light guide connector 19a, and entered in the light source apparatus 11.

The lighting lens 25 condenses light exited from the light guide device 27 downstream of the light source apparatus 11, and applies the light to an object of interest in the body cavity. The objective lens 26 receives and condenses reflected light from the object of interest, such as body tissue, and forms an optical image. An image sensor is positioned at a point of focusing of the objective lens 26 for generating an image signal by imaging the object, namely the complementary color image sensor 28 for the first endoscope 13a, the three primary color image sensor 29 for the second endoscope 13b, and the monochromatic image sensor 30 for the third endoscope 13c. A preferable example of the image sensor is a CCD image sensor (charge coupled device image sensor).

Figure 4:
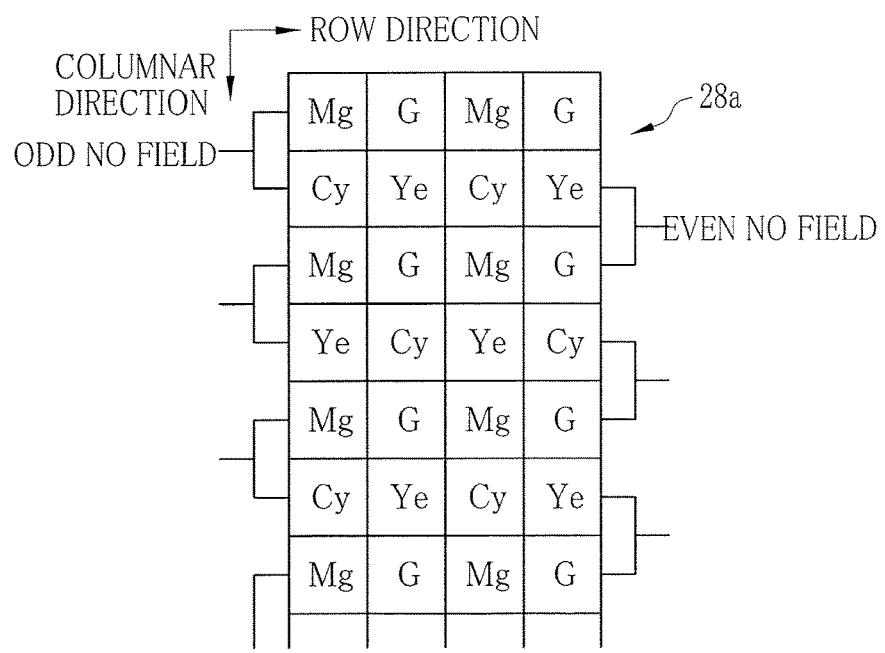
FIG. 4 is an explanatory view in a plan, illustrating a complementary color separation filter or first separation filter.

A complementary color separation filter 28a or first separation filter is disposed on an imaging surface of the complementary color image sensor 28. In FIG. 4, the complementary color separation filter 28a includes magenta (Mg), green (G), cyan (Cy) and yellow (Y) color filter segments arranged at pixels. In short, the complementary color image sensor 28 has magenta, green, cyan and yellow pixels. Among those, magenta, cyan, magenta and yellow pixels are arranged cyclically in pixel columns of odd numbers. Green, yellow, green and cyan pixels are arranged cyclically in pixel columns of even numbers. Magenta and green pixels are arranged alternately in pixel rows of odd numbers. Cyan and yellow pixels are arranged alternately in pixel rows of even numbers. Arrangement of those color filters is referred to as line-sequential color difference arrangement or complementary interlace.

Figure 5:
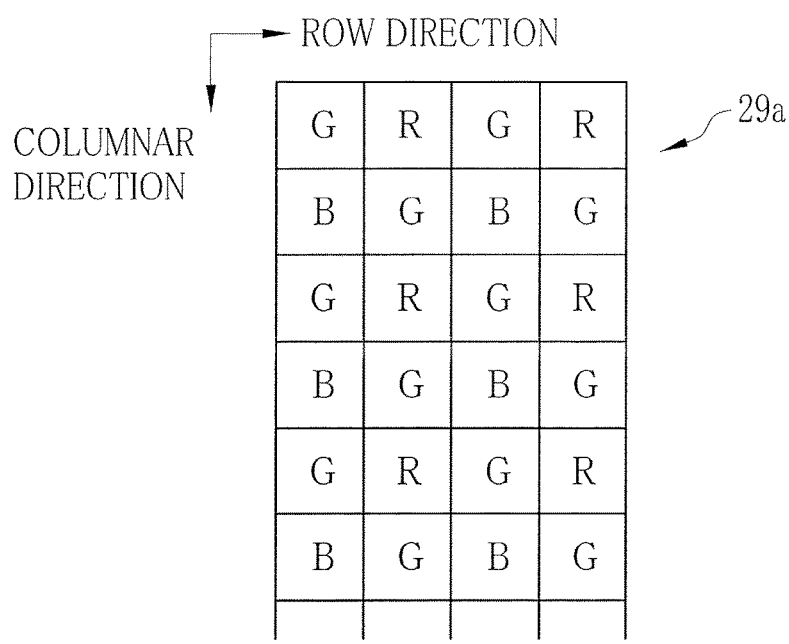
FIG. 5 is an explanatory view in a plan, illustrating a three primary color separation filter or second separation filter.

A three primary color separation filter 29a or second separation filter is disposed on an imaging surface of the three primary color image sensor 29. In FIG. 5, the three primary color separation filter 29a includes red (R), green (G) and blue (B) color filter segments arranged at pixels. In short, the three primary color image sensor 29 has red, green and blue pixels. Among those, green and blue pixels are arranged alternately in pixel columns of odd numbers. Red and green pixels are arranged alternately in pixel columns of even numbers. Green and red pixels are arranged alternately in pixel rows of odd numbers. Blue and green pixels are arranged alternately in pixel rows of even numbers. Arrangement of those color filters is referred to as primary color Bayer arrangement.

Note that the monochromatic image sensor 30 does not have a color separation filter. There is no difference between the pixels in spectral sensitivity.

A flash memory or storage medium 31 as non-volatile memory is incorporated in the endoscope 13, and stores property information of the endoscope 13, for example, information of color filter arrangement of the image sensor, pixel number of its pixels and the like.

The processing apparatus 12 includes a controller 32 (master controller), an imaging control unit 33, a correlation double sampler 34 (CDS), an A/D converter 35, a brightness detector 36, a light adjuster 37, an image signal processor 38 and a channel allocator 39.

The controller 32 controls various elements in the processing apparatus 12 and the light source apparatus 11. In response to connection of the endoscope 13 to the light source apparatus 11 and the processing apparatus 12, the controller 32 reads the property information from the storage medium 31, to recognize the type of the endoscope 13 in connection. The controller 32 controls the imaging control unit 33 according to the type of the endoscope 13, and drives the image sensor.

The imaging control unit 33, in case the first endoscope 13a is used as the endoscope 13, drives the complementary color image sensor 28 in the first endoscope 13a in a method of field readout according to an emission time point of the light source apparatus 11. In the field readout, pixel signals of pixels of two pixel rows are mixed (added up) in relation to two pixels adjacent in a columnar direction at the time of readout in the odd number field and even number field. See FIG. 4. The mixture of the pixel signals is performed in a horizontal transfer path (not shown) in the CCD image sensor.

Figure 6:
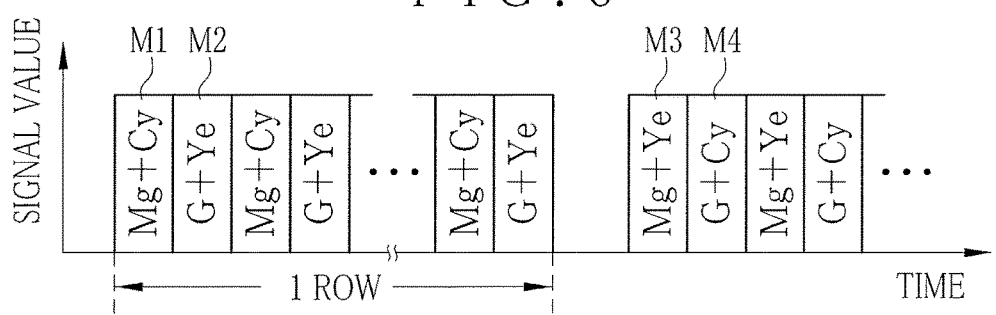
FIG. 6 is a timing chart illustrating an output signal from a complementary color image sensor.

According to the field readout, the complementary color image sensor 28 outputs first to fourth mixture pixel signals M1-M4 for each of the odd number field and even number field as illustrated in FIG. 6. The first mixture pixel signal M1 is a mixture pixel signal of a magenta pixel and a cyan pixel. The second mixture pixel signal M2 is a mixture pixel signal of a green pixel and a yellow pixel. The third mixture pixel signal M3 is a mixture pixel signal of a magenta pixel and a yellow pixel. The fourth mixture pixel signal M4 is a mixture pixel signal of a green pixel and a cyan pixel.

Assuming that the endoscope 13 is the second endoscope 13b, the imaging control unit 33 drives the three primary color image sensor 29 in the second endoscope 13b in a well-known method of progressive readout according to an emission time point of the light source apparatus 11. In the progressive readout, a pixel signal of one frame is read out discretely by one pixel row without mixture of a pixel signal.

Assuming that the endoscope 13 is the third endoscope 13c, the imaging control unit 33 drives the monochromatic image sensor 30 in the third endoscope 13c in the progressive readout according to an emission time point of the light source apparatus 11, in a manner similar to the three primary color image sensor 29.

Also, the controller 32 receives a mode selection signal input by operation of the mode selector 17a of the endoscope 13, and controls the light source controller 21 according to one of the imaging modes specified by the mode selection signal and the type of the endoscope 13. One of the lighting controls of the light source apparatus 11 is selected by the controller 32 according to the data table of FIG. 7.

In the use of the first endoscope 13a among the types of the endoscope 13 and in the normal imaging mode, blue light BL, green light GL and red light RL are emitted simultaneously in FIG. 8. Readout of the odd number field and even number field is performed during the emission of the light. An image of one frame is produced from the odd number field and even number field of the readout.

Figure 9:
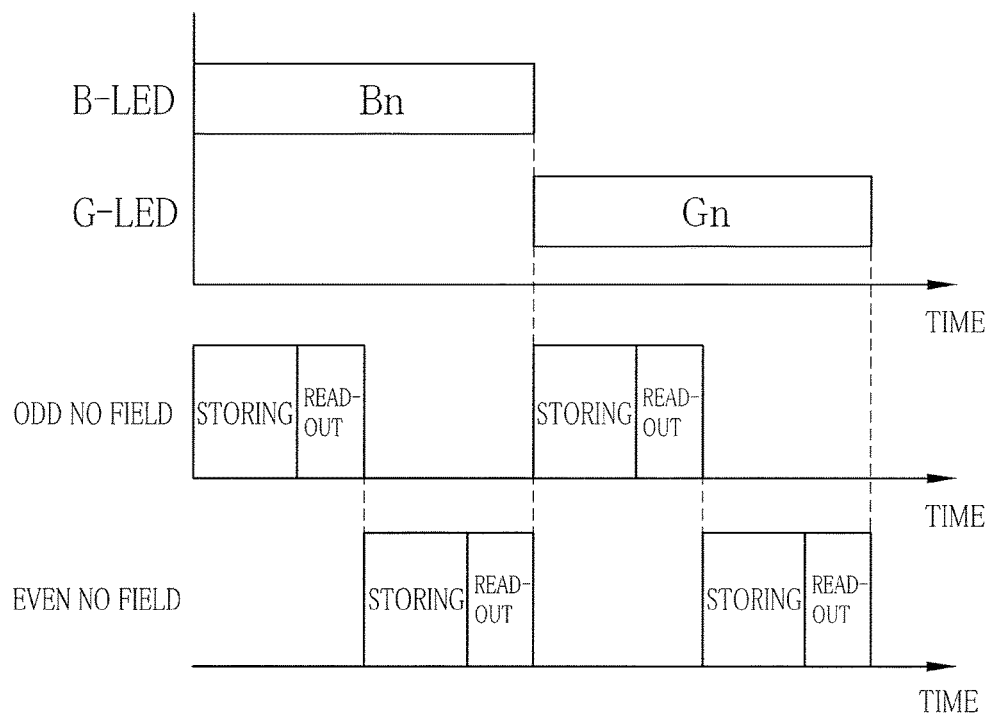
FIG. 9 is a timing chart illustrating a sequence of driving for narrow band imaging.

In the use of the first endoscope 13a and in the narrow band imaging mode, narrow band blue light Bn and narrow band green light Gn are emitted simultaneously in FIG. 9. Readout of the odd number field and even number field is performed during the emission of the light. An image of one frame is produced from the odd number field and even number field of the readout.

Assuming that the second endoscope 13b is used for the endoscope 13, the simultaneous lighting is used irrespective of the imaging mode. In case the third endoscope 13c is used for the endoscope 13, the field sequential lighting is used irrespective of the imaging mode. The time sequence of emission of FIGS. 8 and 9 is repeated except for the difference in the number of the light components.

Signals from the complementary color image sensor 28, the three primary color image sensor 29 and the monochromatic image sensor 30 are input to the CDS 34. The CDS 34 eliminates noise components from the signals due to the CCD image sensor by performing the correlation double sampling. The signal after the noise elimination in the CDS 34 is supplied to the A/D converter 35, and also output to the brightness detector 36. The A/D converter 35 converts the signal into a digital signal, which is supplied to the image signal processor 38.

The brightness detector 36 detects brightness of an object of interest according to a signal input by the CDS 34, namely an average brightness of the input signal. The light adjuster 37 produces an adjustment signal by subtraction of the brightness signal from the brightness detector 36 from a reference brightness or target value of the light adjustment. The light source controller 21 is supplied with the adjustment signal. The light source controller 21 controls light intensity of the plural LEDs in the LED light source 20 to regulate a light amount of the light so as to obtain the reference brightness.

The image signal processor 38 includes a selector 40, a first processing unit 41, a second processing unit 42, a third processing unit 43 and an image memory 44. The selector 40 selects one of the processing units according to the type of the endoscope 13 recognized by the controller 32.

Figure 10:
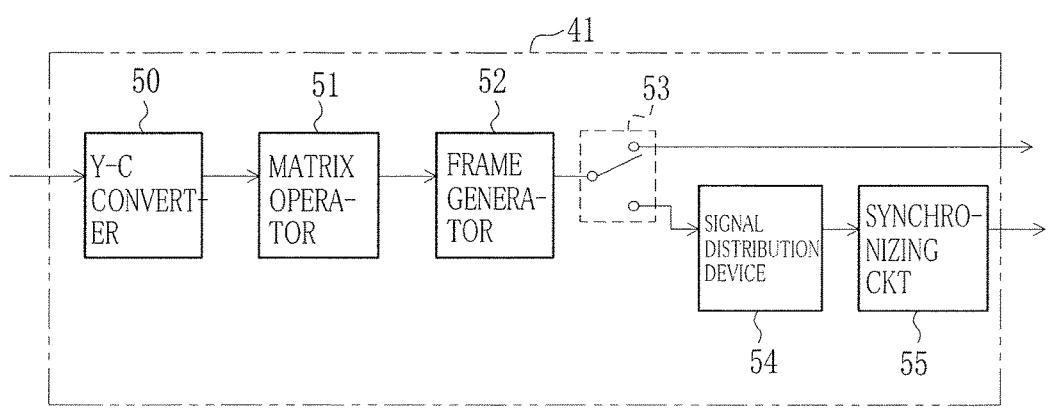
FIG. 10 is a block diagram schematically illustrating a first processing unit for a first endoscope.

In FIG. 10, the first processing unit 41 includes a Y-C converter 50, a matrix operator 51, a frame generator 52, a switch 53, a signal distribution device 54 and a synchronizing circuit 55 for synchronization processing. The first to fourth mixture pixel signals M1-M4 are sequentially input to the Y-C converter 50 by the complementary color image sensor 28 in the first endoscope 13*a* and through the CDS 34 and the A/D converter 35.

The Y-C converter 50 operates for Y-C conversion according to well-known arithmetic operations for use in the line-sequential color difference arrangement or complementary interlace, and produces a luminance signal Y and chrominance signals Cr and Cb. Those are determined by addition or subtraction between the first and second mixture pixel signals M1 and M2 adjacent with one another in the row direction, and by addition or subtraction between the third and fourth mixture pixel signals M3 and M4 adjacent with one another in the row direction.

The matrix operator 51 performs a predetermined matrix operation for the luminance signal Y and chrominance signals Cr and Cb from the Y-C converter 50, and produces RGB signals. The Y-C converter 50 and the matrix operator 51 operate for each of the odd number field and even number field in relation to the Y-C conversion and the matrix operation.

The frame generator 52 generates image data of one frame according to RGB signals obtained for each one of the odd number field and even number field. To this end, interpolation is performed by use of plural adjacent pixels (for example, eight pixels next to a target pixel) for producing RGB signals according to pixels of image data of one frame.

The switch 53 is controlled by the controller 32 and changes over an output destination of image data produced by the frame generator 52. Incase the lighting is the simultaneous lighting, the switch 53 specifies the image memory 44 for an output destination, and transmits the image data from the frame generator 52 to the image memory 44. In FIG. 8, the red light RL, green light GL and blue light BL are emitted simultaneously in a period of one frame in the simultaneous lighting. RGB signals in the image data transmitted to the image memory 44 include components of all the colors.

Figure 11:
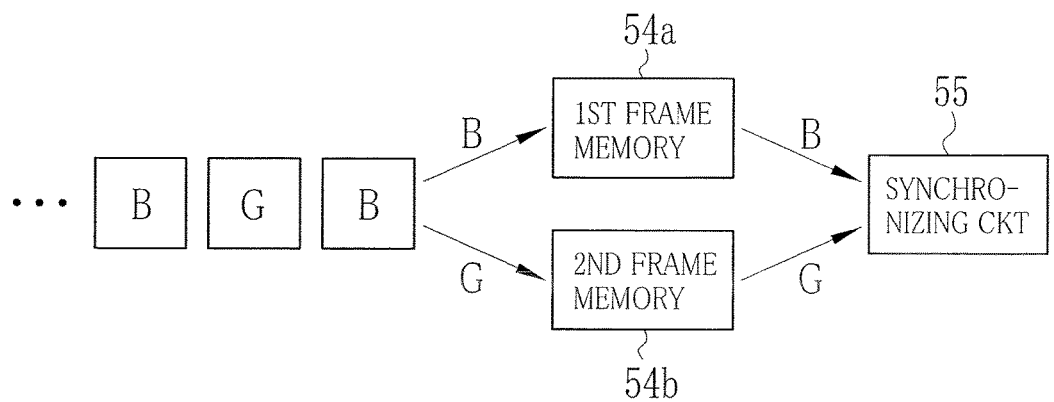
FIG. 11 is a block diagram schematically illustrating a signal distribution device.

In case lighting is the field sequential lighting, the switch 53 sets an output designation of the signal distribution device 54, and sends the image data to the signal distribution device 54 from the frame generator 52. In FIG. 11, the signal distribution device 54 includes first and second frame memories 54*a* and 54*b*. Signal components in the image data in the period of the two consecutive frames from the frame generator 52 are cyclically distributed to and stored in the first and second frame memories 54*a* and 54*b*.

In the field sequential lighting, the narrow band blue light Bn and the narrow band green light Gn are emitted alternately in a period of one frame. The signal distribution device 54 distributes a blue signal component (blue image data) from image data according to lighting with the narrow band blue light Bn to the first frame memory 54*a* and writes this to the first frame memory 54*a*, and distributes a green signal component (green image data) from image data according to lighting with the narrow band green light Gn to the second frame memory 54*b* and writes this to the second frame memory 54*b*.

Figure 12:
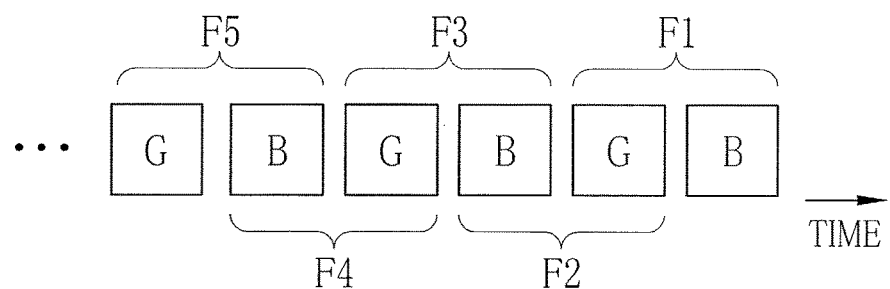
FIG. 12 is a timing chart illustrating a synchronizing circuit.

At each time of updating image data, namely, storing image data of one frame to any one of the first and second frame memories 54*a* and 54*b*, the synchronizing circuit 55 produces image data of a special image of one frame by combining the blue and green image data, and writes the image data to the image memory 44. In FIG. 12, blue and green image data are synchronized by the synchronizing circuit 55 at each time of production of the blue or green image data in the frame generator 52, to produce image data F1, F2, F3 and so on. The image data F1, F2, F3 and so on are produced at a frame rate equal to that in the simultaneous lighting.

Pixel signals for R, G and B pixels are sequentially input to the second processing unit 42 by the three primary color image sensor 29 (or second multi-color image sensor) in the second endoscope 13*b* through the CDS 34 and the A/D converter 35. The second processing unit 42 performs interpolation of plural adjacent pixels (for example, eight pixels next to a target pixel) for producing image data of a normal image of one frame by producing RGB signals. In the narrow band imaging mode, image data of a special image is produced only by use of the B and G signals. The image data from the second processing unit 42 is written to the image memory 44.

The third processing unit 43 is supplied with a pixel signal by the monochromatic image sensor 30 in the third endoscope 13*c* through the CDS 34 and the A/D converter 35. The third processing unit 43 has a signal distribution device and a synchronizing circuit (both not shown) similar to the signal distribution device 54 and the synchronizing circuit 55 in the first processing unit 41.

In the normal imaging mode, the signal distribution device distributes blue, green and red image data respectively to the frame memories according to lighting with the blue light BL, green light GL and red light RL. The signal distribution device inputs those image data to the synchronizing circuit simultaneously. In the narrow band imaging mode, the signal distribution device distributes blue and green image data respectively to the frame memories according to lighting with the narrow band blue light Bn and narrow band green light Gn. The signal distribution device inputs those image data to the synchronizing circuit simultaneously. The synchronizing circuit synchronizes the plural input image data to obtain image data of one frame, which is written to the image memory 44.

The channel allocator 39 allocates image data from the image memory 44 to each one of the channels of the display panel 14 for displaying an image of the image data. In the normal imaging mode, the RGB signals of pixels of the image data are allocated to the R, G and B channels of the display panel 14 for displaying a normal image. In the narrow band imaging mode, a blue signal in the image data is allocated to the B and G channels, and a green signal in the image data is allocated to the G channel, for displaying a special image.

Figure 13:
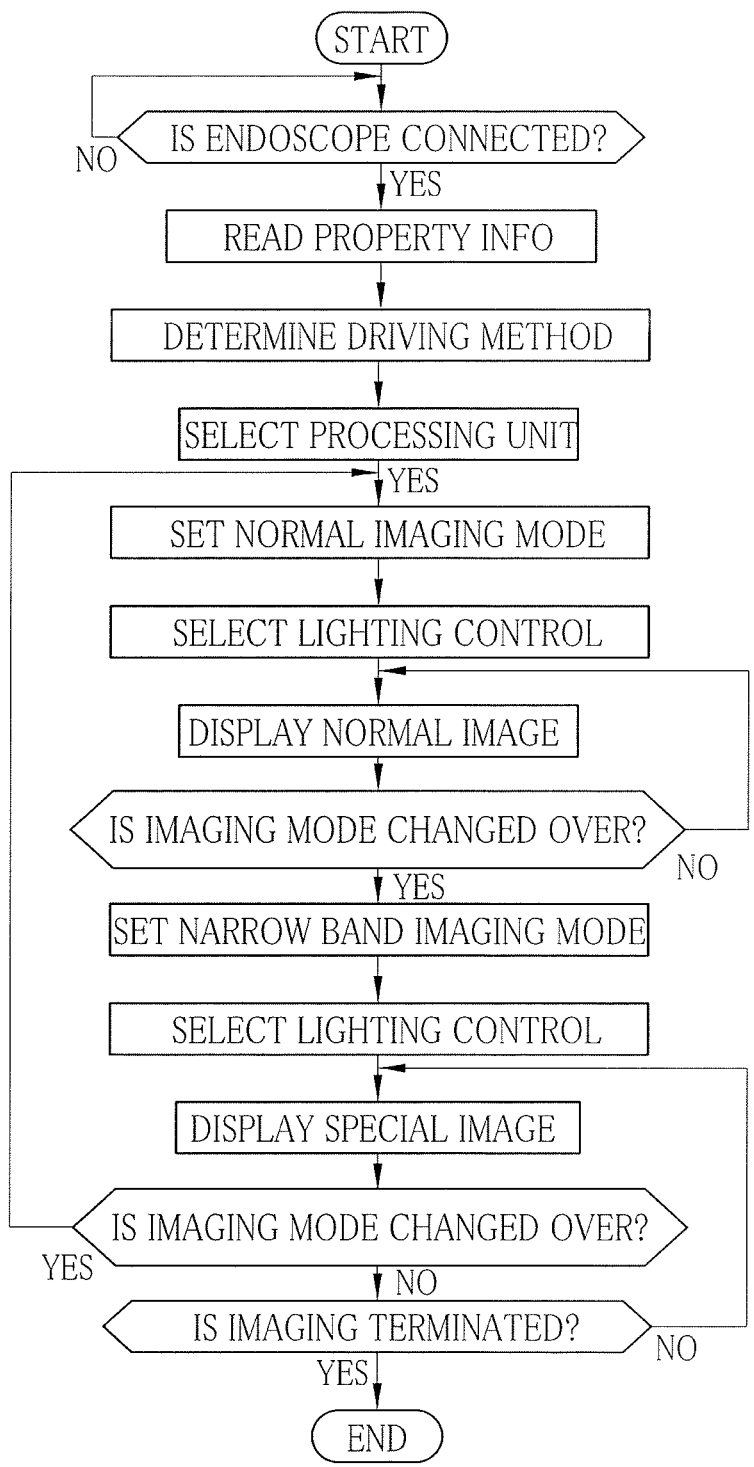
FIG. 13 is a flow chart illustrating operation of the endoscope system.

The operation of the endoscope system 10 is described now with FIG. 13. A physician or operator connects the endoscope 13 to the light source apparatus 11 and the processing apparatus 12. Responsively the controller 32 in the processing apparatus 12 reads property information from the storage medium 31 in the endoscope 13. The controller 32 recognizes a connected type of the endoscope 13 according to the property information, and determines a driving method for readout of the image sensor. The selector 40 in the image signal processor 38 is controlled by the controller 32 to select one of the processing units 41-43 in association with the type of the endoscope 13.

The controller 32 sets the normal imaging mode for the light source apparatus 11 and the processing apparatus 12, and selects a lighting control according to the type and the imaging mode of the endoscope 13 by referring to the data table of FIG. 7. In the use of the first or second endoscope 13a or 13b, the simultaneous lighting is selected. In the use of the third endoscope 13c, the field sequential lighting is selected. The light source apparatus 11 generates light for illumination according to the selected lighting control. An object of interest in a body cavity is irradiated by light emitted through the tip of the endoscope 13, and imaged by the image sensor. A signal is output by the image sensor, and processed by the selected processor according to the selector 40 as described heretofore, to produce image data of a normal image. The display panel 14 is caused to display the normal image by the channel allocator 39. The normal image in the display panel 14 is a result of imaging according to lighting with normal light.

A physician or operator enters the elongated tube 16 of the endoscope 13 in a body cavity for endoscopic imaging. In case he or she wishes to observe a condition of surface blood vessels of body tissue of an object of interest, the mode selector 17a is operated for changeover. An input signal from the mode selector 17a is received by the controller 32, which sets the light source apparatus 11 and the processing apparatus 12 in the narrow band imaging mode.

Upon setting the narrow band imaging mode, a lighting control according to the type and the imaging mode of the endoscope 13 is selected by referring to a data table of FIG. 7. To be precise, the field sequential lighting is set for the first and third endoscopes 13a and 13c. The simultaneous lighting is set for the second endoscope 13b. In a manner similar to the normal imaging mode, lighting and imaging of an object are performed through the tip of the endoscope 13. A signal is outputted by the image sensor, and processed by a processing unit selected by the selector 40 to obtain image data of a special image, which is displayed by the display panel 14 through the channel allocator 39. The display panel 14 operates for displaying the special image according to lighting of the narrow band light.

Displaying the special image is repeated until the mode selector 17a is operated or until the user input interface 15 is manipulated for terminating the imaging. Upon operating the mode selector 17a, the normal imaging mode is set again. Upon operating the user input interface 15 for termination, the imaging is terminated.

As described heretofore, lighting in the narrow band imaging mode is set as the field sequential lighting upon connecting the first endoscope 13a having the complementary color image sensor 28 (or first multi-color image sensor) to the light source apparatus 11 and the processing apparatus 12. The imaging is performed by the complementary color image sensor 28 discretely for the narrow band blue light Bn and narrow band green light Gn. Color separation between blue and green components can be distinct in image data from the first processing unit 41. Color mixture can be decreased.

In the above embodiments, the complementary color image sensor 28 in the first endoscope 13a has a lower sensitivity to narrow band blue light Bn than to narrow band green light Gn. Assuming that brightness of an object of interest is low, visual recognition may be poor because of a low level of a blue signal component of a special image. It is thus possible for the controller 32 to respond to change-over to the narrow band imaging mode by connection of the first endoscope 13a to the light source apparatus 11 and the processing apparatus 12, and to control the light source controller 21 (controller) to set a light amount of the narrow band blue light Bn higher than that of the narrow band green light Gn. To this end, light intensity and/or emission time of the blue and green LEDs 20a and 20b is adjusted to control the light amounts of the narrow band blue light Bn and narrow band green light Gn.

Figure 14:
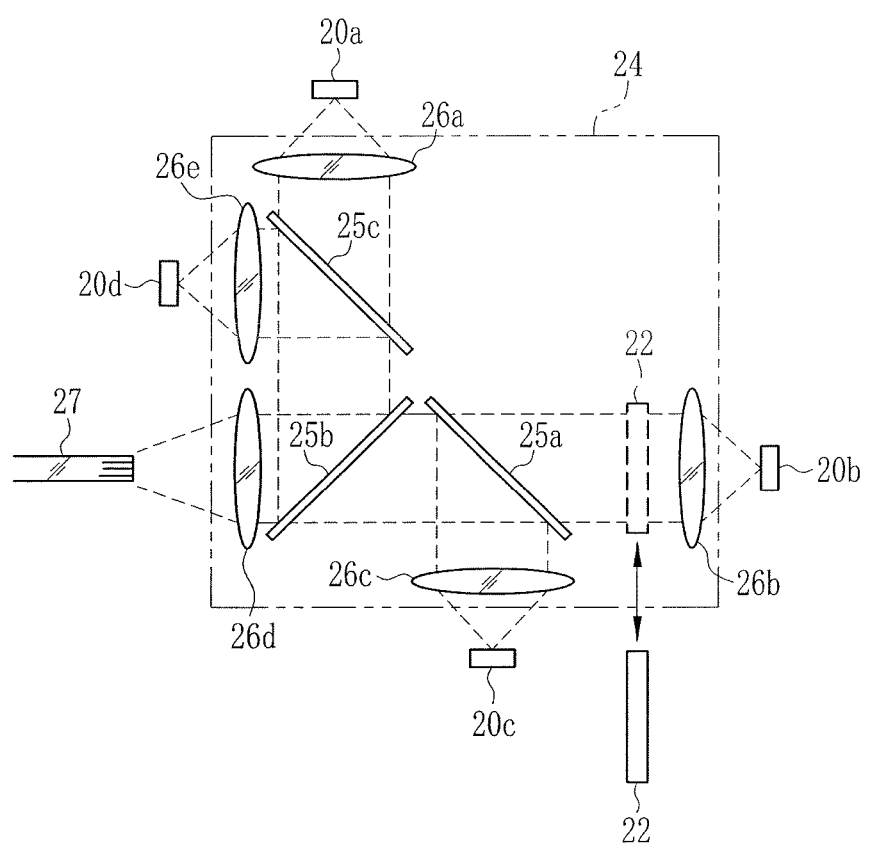
FIG. 14 is a side elevation illustrating another preferred light source apparatus having a second blue LED.

In FIG. 14, another preferred example of the light source apparatus 11 for increasing a light amount of the narrow band blue light Bn. A second blue LED 20d (as light source device), a third dichroic mirror 25c (DM) and a fifth lens 26e are added in the light source apparatus 11. First blue light BL emitted by the blue LED 20a is combined with second blue light BL' emitted by the second blue LED 20d, to produce narrow band blue light Bn of a high light amount. The second blue LED 20d is turned on upon connecting the first endoscope 13a to the light source apparatus 11 and the processing apparatus 12 and upon changeover to the narrow band imaging mode. An example of a wavelength range of the first blue light BL is 450-490 nm. An example of a wavelength range of the second blue light BL' is 380-440 nm.

Second Preferred Embodiment

Figure 15:
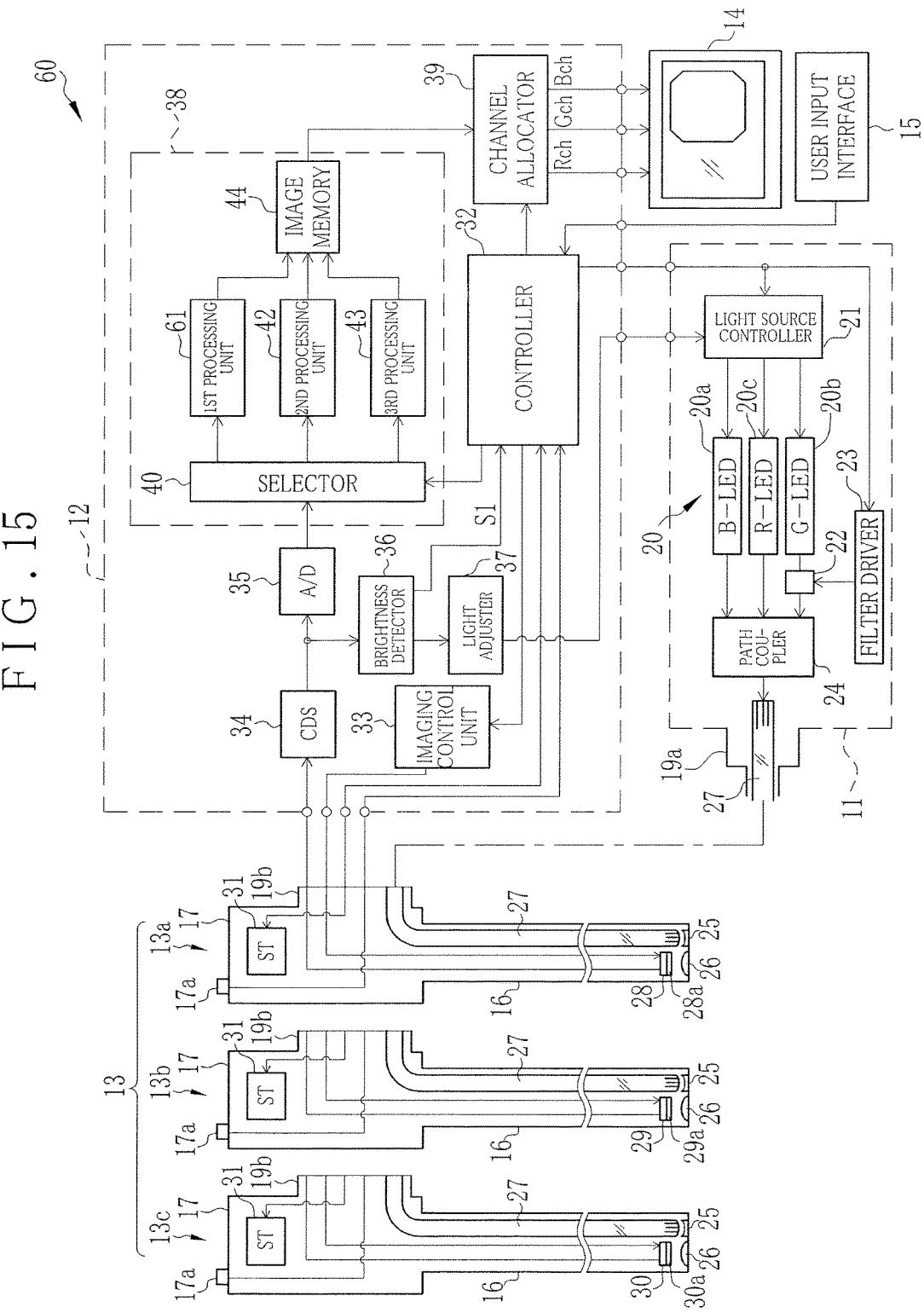
FIG. 15 is a block diagram schematically illustrating an endoscope system.

In FIG. 15, another preferred endoscope system 60 is illustrated. The brightness detector 36 inputs brightness information S1 to the controller 32, namely, the average brightness. While the first endoscope 13a is used in the narrow band imaging mode, the controller 32 changes an emission sequence of the LED light source 20 according to the brightness information S1.

Figure 16:
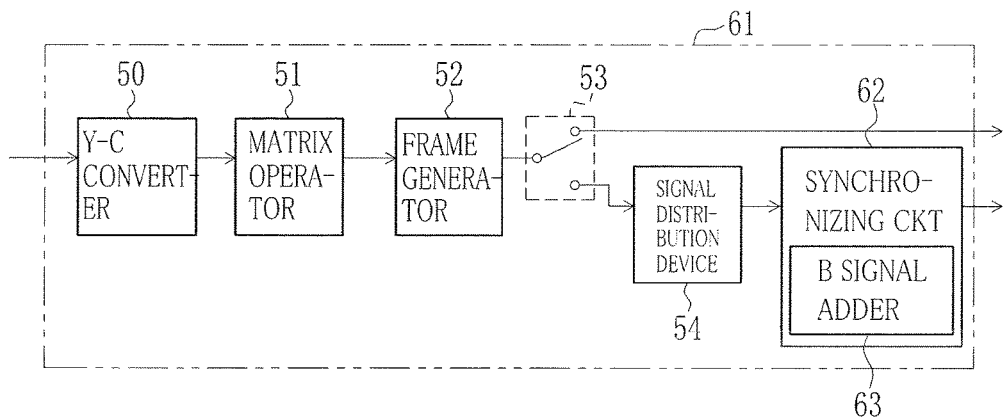
FIG. 16 is a block diagram schematically illustrating a first processing unit for the first endoscope.

In FIG. 16, a first processing unit 61 for the first endoscope is incorporated in the image signal processor 38. The first processing unit 61 has a synchronizing circuit 62 for synchronization processing, and a blue signal adder 63 disposed in the synchronizing circuit 62. Except for those elements, the endoscope system 10 is repeated in the endoscope system 60.

In the embodiment, the controller 32 controls the light source controller 21 according to the brightness information S1 of the object of interest from the brightness detector 36. Assuming that the brightness is higher than the reference brightness, the controller 32 sets the first emission sequence of FIG. 11 for alternately emitting the narrow band blue light Bn and the narrow band green light Gn in a manner similar to the first embodiment. Assuming that the brightness is equal to or lower than the reference brightness, the controller 32 sets a second emission sequence of FIG. 18 for alternately performing two events of emission of the narrow band blue light Bn and one event of emission of the narrow band green light Gn.

Figure 17:
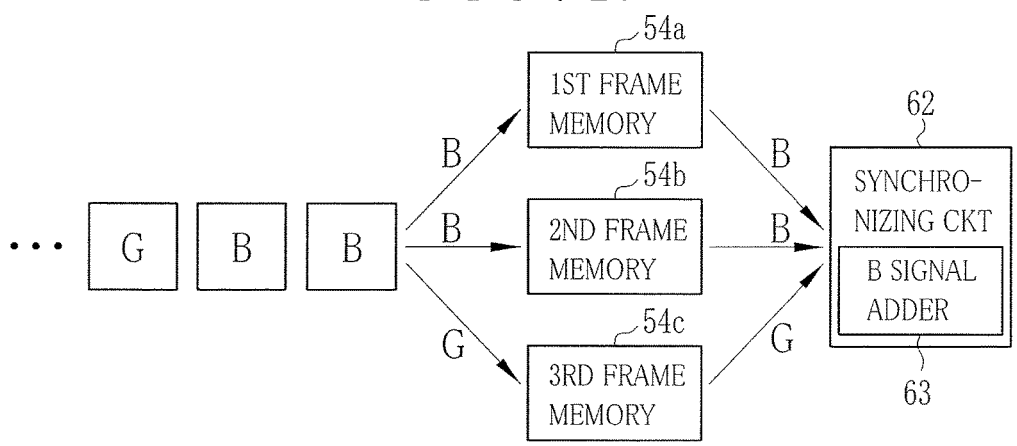
FIG. 17 is a block diagram schematically illustrating a signal distribution device.

In FIG. 17, the signal distribution device 54 in the first processing unit 61 in the second emission sequence distributes two blue image data to the first and second frame memories 54a and 54b and writes the same to those, the image data being produced according to lighting with narrow band blue light Bn of two consecutive events of emission. The signal distribution device 54 distributes green image data to a third frame memory 54c and writes the same thereto, the image data being produced according to lighting with narrow band green light Gn.

Figure 18:
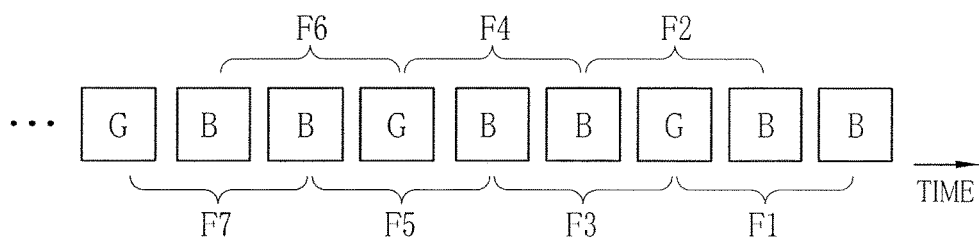
FIG. 18 is a timing chart illustrating a synchronizing circuit.

At each time of updating image data, namely, storing image data of one frame to any one of the frame memories 54a-54c, the blue signal adder 63 adds up a B signal of blue image data of two frames stored in the first and second frame memories 54a and 54b. The synchronizing circuit 62 produces image data of a special image of one frame by combining blue image data according to the added B signal from the blue signal adder 63 and green image data stored in the third frame memory 54c, and writes the image data to the image memory 44. In FIG. 18, two blue image data and one green image data are synchronized at each time of production of blue or green image data in the frame generator 52, to produce image data F1, F2, F3 and so on. The image data F1, F2, F3 and so on are produced at a frame rate equal to that in the simultaneous lighting.

For the signal distribution and synchronization in the first emission sequence, the feature of the first embodiment is repeated. It is also possible to set a light amount of narrow band blue light Bn higher than that of narrow band green light Gn in the first emission sequence as described above.

In the present embodiment, the blue signals of two frames are added up by changing the emission sequence assuming that the brightness of the object of interest is equal to or lower than the reference brightness. Consequently, visual recognition can be higher upon an increase in the components of the blue signals of the special image.

Third Preferred Embodiment

Figure 19:
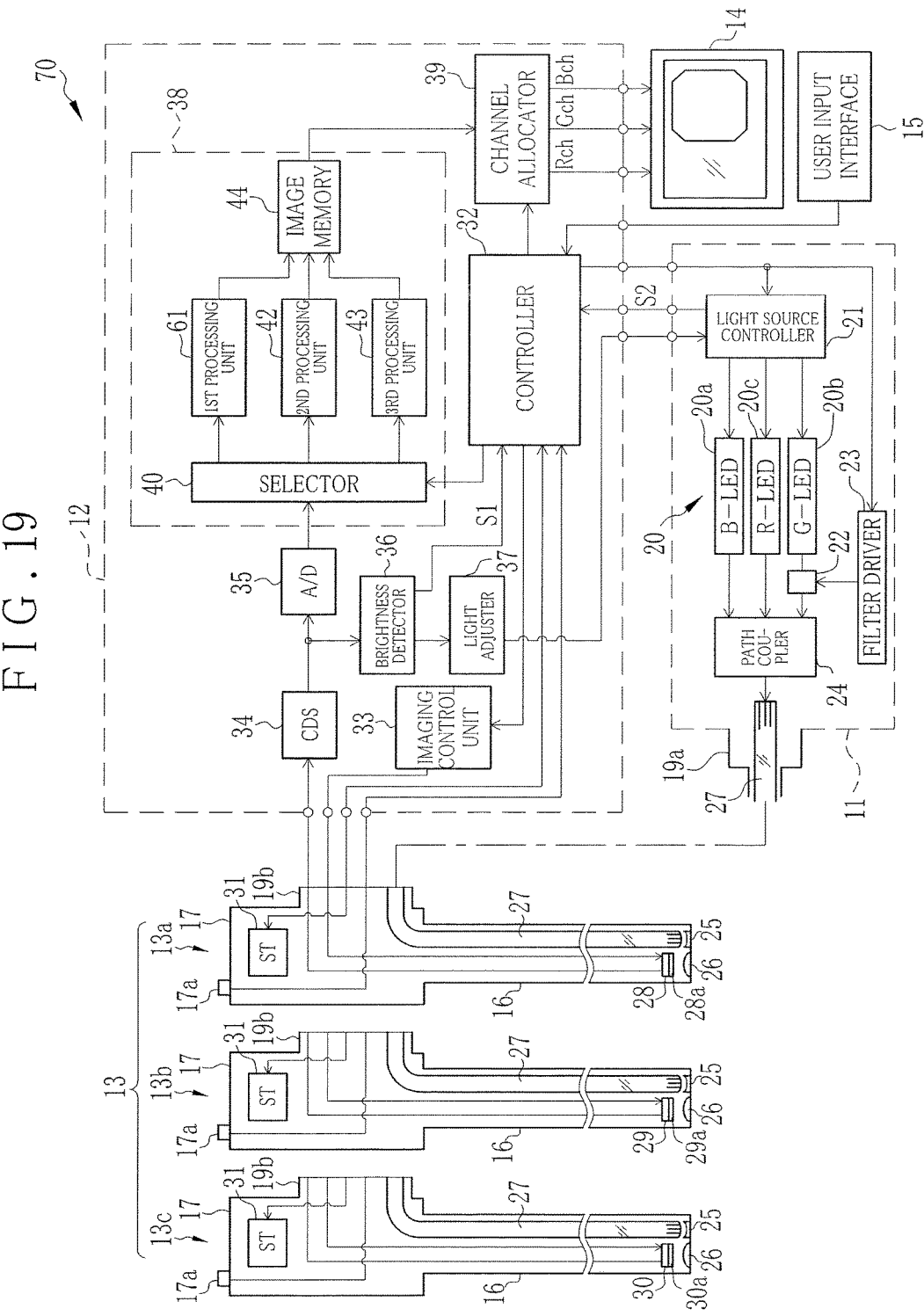
FIG. 19 is a block diagram schematically illustrating still another preferred endoscope system in which a peak intensity of light is utilized.

In FIG. 19, a third preferred endoscope system 70 is illustrated. A control signal of the LED light source 20 controlled by the light source controller 21 is fed back to the controller 32 (master controller). The light source controller 21 controls the light intensity of the LED light source 20 according to an adjustment signal from the light adjuster 37. While the first endoscope 13a is used in the narrow band imaging mode, the light intensity of the LED light source 20 may become the highest as peak intensity. Then the light source controller 21 sends a peak signal S2 to the controller 32.

In case the light intensity of the LED light source 20 becomes the highest as peak intensity, a light amount of the light cannot be increased any more even with shortage in the brightness of the object of interest. Visual recognition of a special image may be low, especially a blue signal component in the special image. In consideration of this, the controller 32 changes over the first emission sequence to the second emission sequence in response to an input of the peak signal S2 from the light source controller 21, in a manner similar to the second embodiment. For the first and second emission sequences, the feature of the second embodiment is repeated. It is preferable to send the peak signal S2 to the controller 32 in case the light intensity of the blue LED 20a included in the LED light source 20 becomes the highest as peak intensity.

Figure 20:
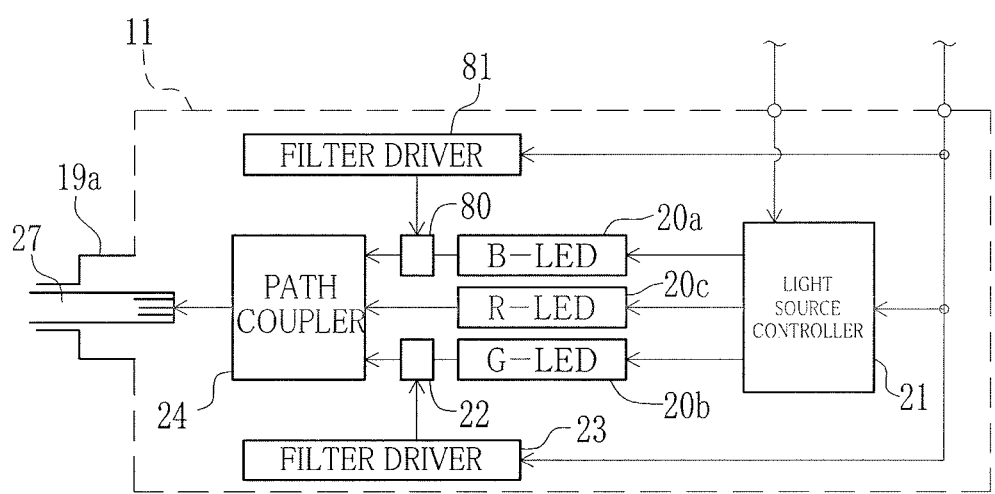
FIG. 20 is a block diagram schematically illustrating another preferred endoscope system having a narrow band blue filter.

In the above embodiments, the blue light BL from the blue LED 20a is used by way of narrow band blue light Bn without change for the narrow band imaging mode. However, it is possible as illustrated in FIG. 20 to add a narrow band blue filter 80 and a filter driver 81 to the light source apparatus 11, typically in consideration of a relatively large wavelength range of the blue light BL.

The narrow band blue filter 80 is moved into and out of a light path of blue light BL from the blue LED 20a by the filter driver 81. In the narrow band imaging mode, the narrow band blue filter 80 is set in the light path of the blue light BL. In the normal imaging mode, the narrow band blue filter 80 is set out of the light path of the blue light BL. In the narrow band imaging mode, the narrow band blue filter 80 produces the narrow band blue light Bn by limiting a wavelength of the blue light BL from the blue LED 20a. Note that the filter driver 81 may be omitted. The filter driver 23 for the narrow band green filter 22 described above can be used additionally for shifting the narrow band blue filter 80 together with the narrow band green filter 22.

Also, the imaging control unit 33, the CDS 34 and the A/D converter 35, although disposed in the processing apparatus 12, may be incorporated in the endoscope 13.

In the above embodiments, the CCD image sensor is used. However, an image sensor according to the invention can be a CMOS image sensor or the like. The CMOS image sensor includes a semiconductor substrate having sensor elements. The imaging control unit 33, the CDS 34, the A/D converter 35 and the like can be mounted on the semiconductor substrate.

In the above embodiments, the light source apparatus 11 has the LED light source 20. However, a laser diode (LD) or the like can be incorporated in the light source apparatus 11 instead of the LEDs of the LED light source 20.

In the above embodiments, the processing apparatus 12 is separate from the light source apparatus 11. However, a composite apparatus inclusive of components of the light source apparatus 11 and the processing apparatus 12 can be used. Also, a component of the light source apparatus 11 can be incorporated in the endoscope 13.

In the above embodiments, the endoscopes of the plural types can be used selectively in the endoscope system. However, an endoscope system of the invention can be constructed specially for use with the first endoscope 13a having the complementary color image sensor 28.

In the above embodiments, the lighting controls are automatically selected for any one of the plural types of the endoscopes in the manner of FIG. 7. However, it is possible in an endoscope system of the invention automatically to select lighting controls only for the first endoscope 13a having the complementary color image sensor 28, and manually to select lighting controls for the remaining types of endoscopes by manipulation of a physician or operator.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. A light source apparatus for endoscopic imaging, comprising:
   a light source for emitting at least first narrow band light and second narrow band light having a longer wavelength than said first narrow band light to illuminate an object in a body cavity, said light source having a field sequential lighting mode and a simultaneous lighting mode, wherein said light source, in said field sequential lighting mode, emits said first narrow band light and said second narrow band light in a discrete manner, and in said simultaneous lighting mode, simultaneously emits said first narrow band light and said second narrow band light;
   a connector connectable with a first endoscope having a complementary color image sensor for imaging said object; and
   a controller for changing said light source between said field sequential lighting mode and said simultaneous lighting mode according to a kind of endoscope connected to said connector, said controller setting said field sequential lighting mode if said first endoscope is connected to said connector and if said light source is used for emitting said first narrow band light and said second narrow band light wherein the controller selectively designates first and second emission sequences in said field sequential lighting, and in said first emission sequence, an event of said first narrow band light and an event of said second narrow band light are alternatively emitted, and in said second emission sequence, two events of emitting said first narrow band light and one event of emitting said second narrow band light are alternately repeated.

2. A light source apparatus as defined in claim 1, wherein said controller operates according to a brightness signal of object brightness of said object, and said object brightness is higher than reference brightness, designates said first emission sequence in said field sequential lighting, and if said object brightness is equal to or lower than said reference brightness, specifies said second emission sequence in said field sequential lighting.

3. A light source apparatus as defined in claim 2, wherein said controller controls light intensity of said light source according to information of a difference between said object brightness and said reference brightness, and if said light intensity comes up to a peak intensity, changes over said field sequential lighting from said first emission sequence to said second emission sequence.

4. A light source apparatus as defined in claim 1, wherein said complementary color image sensor has pixels of at least yellow, magenta and cyan colors.

5. A light source apparatus as defined in claim 1, wherein said first narrow band light is narrow band blue light, and said second narrow band light is narrow band green light.

\* \* \* \* \*